(12) United States Patent
Powers, III et al.

(10) Patent No.: US 11,961,332 B1
(45) Date of Patent: Apr. 16, 2024

(54) ELECTRONIC DEVICES WITH 6 MINUTE WALK DISTANCE ESTIMATES

(71) Applicant: Apple Inc., Cupertino, CA (US)

(72) Inventors: William R. Powers, III, San Francisco, CA (US); Maryam Etezadi-Amoli, Santa Clara, CA (US); Britni A. Crocker, Campbell, CA (US); Allison L. Gilmore, Redwood City, CA (US); Edith M. Arnold, San Francisco, CA (US); Hung A. Pham, Sunnyvale, CA (US); Irida Mance, San Francisco, CA (US); Sumayah F. Rahman, Mountain View, CA (US); Katherine Niehaus, San Francisco, CA (US); Kyle A. Reed, San Jose, CA (US); Maxsim L. Gibiansky, Sunnyvale, CA (US); Karthik Jayaraman Raghuram, Foster City, CA (US); Adeeti V. Ullal, Emerald Hills, CA (US)

(73) Assignee: Apple Inc., Cupertino, CA (US)

( * ) Notice: Subject to any disclaimer, the term of this patent is extended or adjusted under 35 U.S.C. 154(b) by 202 days.

(21) Appl. No.: 17/338,499

(22) Filed: Jun. 3, 2021

Related U.S. Application Data

(60) Provisional application No. 63/041,731, filed on Jun. 19, 2020.

(51) Int. Cl.
  *G06V 40/20* (2022.01)
  *A61B 5/00* (2006.01)
  *A61B 5/11* (2006.01)

(52) U.S. Cl.
  CPC ............ *G06V 40/25* (2022.01); *A61B 5/1118* (2013.01); *A61B 5/1123* (2013.01); *A61B 5/6802* (2013.01); *A61B 2562/0219* (2013.01)

(58) Field of Classification Search
  CPC ..... G06V 40/25; A61B 5/1118; A61B 5/1123; A61B 5/6802; A61B 2562/0219;
  (Continued)

(56) References Cited

U.S. PATENT DOCUMENTS 8,140,154 B2    3/2012  Donnelly et al.
9,137,309 B2 *  9/2015  Ananny .............. G01C 22/006
(Continued)

FOREIGN PATENT DOCUMENTS

CN    103212197      *  7/2013
EP    3136269 A1    *  3/2017  ........... A61B 5/0205
(Continued)

OTHER PUBLICATIONS

Machine Translation of CN-103212197, Patent Translate, pp. 1-91, printed on Apr. 18, 2023 (Year: 2013).*
(Continued)

*Primary Examiner* — Yi-Shan Yang
*Assistant Examiner* — Om Patel
(74) *Attorney, Agent, or Firm* — Treyz Law Group, P.C.; David K. Cole

(57) ABSTRACT

One or more electronic device may use motion and/or activity sensors to estimate a user's 6 minute walking distance. In particular, because users typically walk at less than their maximum output and in imperfect conditions, control circuitry within the device(s) may rely on walks of shorter distances to estimate the 6 minute walking distance. For example, the control circuitry may gather activity information for the user, such as heart rate, calories burned, and step count, and analyze a distance component and a speed component for periods in which the user has walked. Individual 6 minute walk distance estimates may be generated based on each of the activity information, distance component, and speed component. The distance and speed esti-
(Continued)

mates may be corrected for walking behaviors that deviate from an ideal testing environment, and may then be fused with the activity estimate to generate a final 6 minute walk distance estimate.

17 Claims, 9 Drawing Sheets

(58) Field of Classification Search
CPC ......... A61B 5/11; A61B 5/112; A61B 5/1121; A61B 5/68; A61B 5/6801; A61B 5/6804; A61B 5/6807; A61B 5/6824; A61B 5/6825; A61B 5/6828–6829; A61B 5/6831; A61B 5/681
See application file for complete search history.

(56) References Cited

U.S. PATENT DOCUMENTS

| | | | |
|---|---|---|---|
| 10,307,111 B2 | 6/2019 | Muhsin et al. | |
| 10,542,933 B2 | 1/2020 | Sato et al. | |
| 10,586,619 B1* | 3/2020 | Richards | G06N 3/08 |
| 10,632,343 B2* | 4/2020 | Meschter | G16Z 99/00 |
| 2010/0298899 A1* | 11/2010 | Donnelly | A61N 1/3987 607/6 |
| 2011/0231101 A1 | 9/2011 | Bidargaddi et al. | |
| 2015/0065893 A1* | 3/2015 | Ye | A61B 5/0205 600/595 |
| 2015/0294440 A1* | 10/2015 | Roberts | G06T 3/40 345/666 |

FOREIGN PATENT DOCUMENTS

| | | | | |
|---|---|---|---|---|
| JP | 6683562 B2 * | 4/2020 | | A61B 5/02 |
| WO | WO-2009023923 A1 * | 2/2009 | | A61B 5/1118 |
| WO | WO-2011028386 A1 * | 3/2011 | | A61B 5/0022 |
| WO | WO-2017011431 A2 * | 1/2017 | | A61B 5/0022 |

OTHER PUBLICATIONS

Machine Translation of JP-6683562-B2, Patent Translate, pp. 1-94, printed on May 2, 2023 (Year: 2020).*

* cited by examiner

ELECTRONIC DEVICES WITH 6 MINUTE WALK DISTANCE ESTIMATES

This application claims the benefit of provisional patent application No. 63/041,731, filed on Jun. 19, 2020, which is hereby incorporated by reference herein in its entirety.

FIELD

This relates generally to electronic devices, and, more particularly, to electronic devices with health sensor and detection circuitry.

BACKGROUND

Electronic devices are often worn or carried near a user's body. The devices may include sensors that are capable of detecting health information, such as heart rate, or movement information, such as distance traveled. One standardized test that is used in diagnostic, clinical settings to determine a person's health is the 6 minute walk distance, in which the person is tested to see how far they can walk in six minutes. There are unique aspects to this test, however, as the test must occur on an unobstructed, flat, track that has 180° turns at each end. Because of the test's prevalence as a prognostic indicator of mortality and health issues, an indicator of cardiac, respiratory, circulatory, and neuromuscular function, an indicator of mortality, and an endpoint of clinical trials and assessing patients with conditions such as chronic obstructive pulmonary disease (COPD) or congestive heart failure (CHF) during rehabilitation, it may be desirable to test people's 6 minute walk distances regularly. However, many people may not walk for six minutes under the ideal conditions required to determine a six minute walk distance. Therefore, it may be desirable to approximate a user's 6 minute walk distance based on their everyday movements using a portable electronic device.

SUMMARY

Electronic devices such as cellular telephone, wristwatches, and other portable devices are often worn or carried by users. The electronic devices may include motion sensors, such as accelerometers, gyroscopes, and/or global positioning system (GPS) sensors, as examples, that may indicate movement of the electronic device. Additionally, the devices may include health sensors, such as heart rate sensors, electrocardiogram sensors, and/or perspiration sensors, as examples, that may indicate activity information of the user.

To estimate a user's 6 minute walk distance, control circuitry within the electronic devices may rely on both the movement of the electronic device and the activity information of the user. In particular, the control circuitry may determine that the user has walked for a period of time based on the movement of the device, and log distance and speed data for that period of time. The activity information of the user may include calories burned by the user, stairs climbed by the user, and any other desired fitness information. The control circuitry may generate estimated 6 minute walking distances based on each of the distance data, the speed data, and the activity information. For example, a shorter walking distance may be extrapolated to approximate the distance that would have been covered in six minutes, or the speed of a user may be used to indicate whether a user could have walked for a longer period of time.

Because of differences between users' general walking behavior and the requirements of the 6 minute walk test when performed in clinical environments, the control circuitry may correct the distance and speed estimates based on various walking behaviors of the user during the respective walking period.

After obtaining the corrected distance and speed 6 minute walk distance estimates, the control circuitry may fuse the distance, speed, and activity based 6 minute walk distances into a final 6 minute walk distance that may be logged for the user.

DETAILED DESCRIPTION

Electronic devices are often carried by users as they conduct their daily activities. For example, a user may carry an electronic device while walking, exercising, or climbing stairs. To provide a user with fitness tracking functionality and other functions, it may be desirable to monitor a user's activities. For example, sensors in an electronic device may monitor user movement (e.g., a user's movement may be inferred from a measured movement of the electronic device). In an illustrative configuration, a motion sensor such as an accelerometer, an altimeter, and/or other sensors in an electronic device may be used in determining when a user has climbed a flight of stairs or performed other physical activities. The same sensors and/or other sensors within the device may be used to determine whether a user has been active or exercised, and the device may track the user's workouts.

To provide a 6 minute walk metric for the user, the device may rely on the motion sensors and other sensors to determine a user's daily activity, distance walked over time, and movement speed. Because the 6 minute walk test requires an unobstructed, flat, track with 180° turns on either end of the track to be used for diagnostic and other purposes, the user's distance and speed may be corrected to account for walking behaviors that depart from these ideal conditions. The corrected distance and speed components may then be fused with the daily activity component to estimate the user's 6 minute walk metric.

Figure 1:
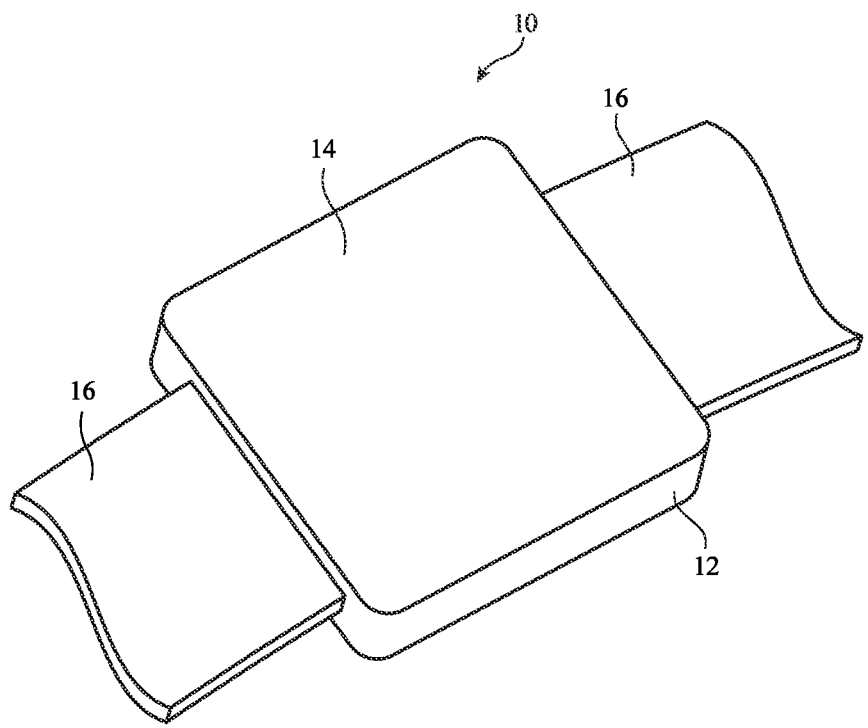
FIG. 1 is a drawing of an illustrative wearable electronic device in accordance with an embodiment.

In general, any suitable electronic devices may be used in measuring the user's motion and activity. As shown in FIG. 1, a wearable electronic device 10, which may be a wristwatch device, may have a housing 12, a display 14, and a strap 16. The wristwatch may attach to a user's wrist via strap 16, and provide skin contact on the user's wrist, by which sensors within device 10 may measure signs of physical exertion, such as increased heart rate and perspiration. Additionally, sensors within housing 12 may be used to determine that the wristwatch, and therefore the user, is moving.

Figure 2:
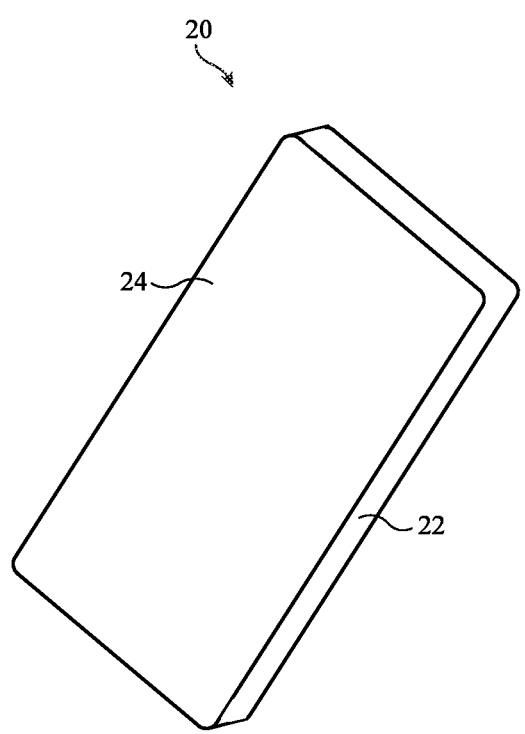
FIG. 2 is a drawing of an illustrative portable device in accordance with an embodiment.

Another illustrative device that may be used to measure the user's motion and activity is shown in FIG. 2. As shown in FIG. 2, a portable device 20, which may be a cellular telephone, for example, has housing 22 and display 24. Sensors within housing 22 may detect motion of the user. In particular, portable device 20 may often be carried in a user's pocket, close to their center of mass, and therefore provide an accurate distance measurement based on movement of the user's legs.

Figure 3:
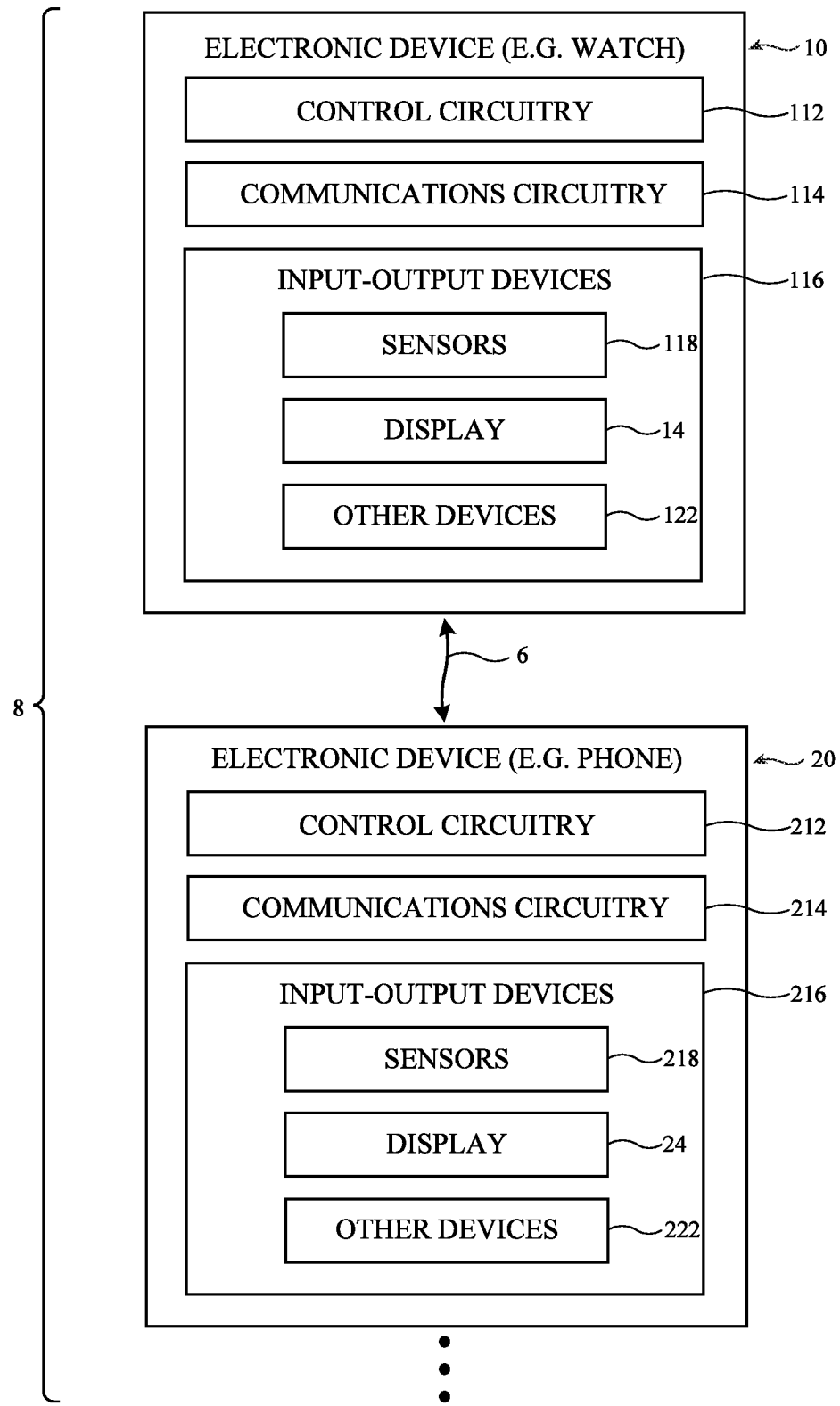
FIG. 3 is a diagram of an illustrative system of two electronic devices in communication with one another in accordance with an embodiment.

Although electronic devices 10 and 20 may be used separately to determine movement and activity of a user, they may also communicate to provide enhanced measurements. As shown in FIG. 3, electronic device 10 and 20, as well as additional electronic devices may be used in system 8, if desired. Device 10 may be, for example, a wristwatch device as shown in FIG. 1, or may be a cellular telephone, a media player, or other handheld or portable electronic device, a wristband device, a pendant device, a headphone, ear bud, or earpiece device, a head-mounted device such as glasses, goggles, a helmet, or other equipment worn on a user's head, or other wearable or miniature device, a navigation device, or other accessory, and/or equipment that implements the functionality of two or more of these devices. Illustrative configurations in which electronic device 10 is a portable electronic device such as cellular telephones, wristwatch, and portable computer may sometimes be described herein as an example.

Similarly, electronic device 20, which is illustrated in FIG. 2 to be a cellular telephone, may also be a cellular telephone, a wristwatch, a media player, or other handheld or portable electronic device, a wristband device, a pendant device, a headphone, ear bud, or earpiece device, a head-mounted device such as glasses, goggles, a helmet, or other equipment worn on a user's head, or other wearable or miniature device, a navigation device, or other accessory, and/or equipment that implements the functionality of two or more of these devices. Electronic device 20 may communicate with electronic device 10 over path 6. In some embodiments, electronic device 20 may be different from electronic device 10. However, this is merely illustrative. The two electronic devices may be similar if desired. Additionally, electronic devices 10 and 20 may be used together, may be used separately, or may be used in combination with any number of additional electronic devices, as desired.

Additionally, system 8 may include any desired number of electronic devices. Although FIG. 3 shows two electronic devices that communicate over path 6, system 8 may include three or more, four or more, five or more devices. In some embodiments, a single electronic device may be used.

As shown in FIG. 3, electronic devices such as electronic device 10 may have control circuitry 112. Control circuitry 112 may include storage and processing circuitry for controlling the operation of device 10. Circuitry 112 may include storage such as hard disk drive storage, nonvolatile memory (e.g., electrically-programmable-read-only memory configured to form a solid-state drive), volatile memory (e.g., static or dynamic random-access-memory), etc. Processing circuitry in control circuitry 112 may be based on one or more microprocessors, microcontrollers, digital signal processors, baseband processors, power management units, audio chips, graphics processing units, application specific integrated circuits, and other integrated circuits. Software code may be stored on storage in circuitry 112 and run on processing circuitry in circuitry 112 to implement control operations for device 10 (e.g., data gathering operations, operations involving the adjustment of the components of device 10 using control signals, etc.).

Electronic device 10 may include wired and wireless communications circuitry. For example, electronic device 10 may include radio-frequency transceiver circuitry 114 such as cellular telephone transceiver circuitry, wireless local area network transceiver circuitry (e.g., WiFi® circuitry), short-range radio-frequency transceiver circuitry that communicates over short distances using ultra high frequency radio waves (e.g., Bluetooth® circuitry operating at 2.4 GHz or other short-range transceiver circuitry), millimeter wave transceiver circuitry, and/or other wireless communications circuitry.

Device 10 may include input-output devices 116. Input-output devices 116 may be used to allow a user to provide device 10 with user input. Input-output devices 116 may also be used to gather information on the environment in which device 10 is operating. Output components in devices 116 may allow device 10 to provide a user with output and may be used to communicate with external electrical equipment.

In some embodiments, the sensors in one of electronic device 10 and electronic device 20 may be used to calibrate the other device. For example, if electronic device 10 is a wearable electronic device and electronic device 20 is a cellular telephone, the motion sensors within electronic device 20 may provide motion data to the wristwatch, which may calibrate its motion sensors based on the motion data from the telephone. This may be beneficial, as the cellular telephone may be carried in a user's pocket, closer to their center of mass, than on the wrist of the user. However, this is merely illustrative. In general, any number of electronic devices in system 8 may generate data that may be communicated to other devices within system 8 and used to calibrate sensors within those other devices. In this way, the accuracy of the devices in the system may be improved, even when the devices are used individually at a later time.

As shown in FIG. 3, input-output devices 116 may include one or more optional displays such as displays 14. Displays 14 may be organic light-emitting diode displays or other displays with light-emitting diodes, liquid crystal displays, or other displays. Displays 14 may be touch sensitive (e.g., displays 14 may include two-dimensional touch sensors for capturing touch input from a user) and/or displays 14 may be insensitive to touch.

Input-output circuitry 116 may include sensors 118. Sensors 118 may include, for example, three-dimensional sensors (e.g., three-dimensional image sensors such as structured light sensors that emit beams of light and that use two-dimensional digital image sensors to gather image data for three-dimensional images from light spots that are produced when a target is illuminated by the beams of light, binocular three-dimensional image sensors that gather three-dimensional images using two or more cameras in a binocular imaging arrangement, three-dimensional lidar (light detection and ranging) sensors, three-dimensional radio-frequency sensors, or other sensors that gather three-dimensional image data), cameras (e.g., infrared and/or visible digital image sensors), gaze tracking sensors (e.g., a gaze tracking system based on an image sensor and, if desired, a light source that emits one or more beams of light that are tracked using the image sensor after reflecting from a user's eyes), touch sensors, capacitive proximity sensors, light-based (optical) proximity sensors, other proximity sensors, force sensors, sensors such as contact sensors based on switches, gas sensors, pressure sensors, moisture sensors, magnetic sensors (such as a magnetometer), audio sensors (such as microphones that may measure a user's breathlessness, as an example), ambient light sensors, microphones for gathering voice commands and other audio input, sensors that are configured to gather information on motion, position, and/or orientation (e.g., accelerometers, gyroscopes, compasses, and/or inertial measurement units that include all of these sensors or a subset of one or two of these sensors), health sensors that measure various biometric information (e.g., heartrate sensors (such as a photoplethysmography sensor), electrocardiogram sensors, and perspiration sensors) and/or other sensors.

User input and other information may be gathered using sensors and other input devices in input-output devices 116. If desired, input-output devices 116 may include other devices 122 such as haptic output devices (e.g., vibrating components), light-emitting diodes and other light sources, speakers such as ear speakers for producing audio output, circuits for receiving wireless power, circuits for transmitting power wirelessly to other devices, batteries and other energy storage devices (e.g., capacitors), joysticks, buttons, and/or other components.

Similarly, electronic device 20 may have control circuitry 212, communication circuitry 214, and input-output devices 216. Input-output devices 216 may include sensors 218, optional display 24, and other devices 222. Control circuitry 212, communication circuitry 214, input-output devices 216, sensors 218, display 24, and other devices 222 may function similarly as described above in regards to the corresponding parts of electronic device 10. However, electronic device 20 may have different configurations of control circuitry, different bands of communications circuitry, and different combinations of sensors, if desired.

During operation, the communications circuitry of the devices in system 8 (e.g., communications circuitry 112 and communications circuitry 212), may be used to support communication between the electronic devices. For example, one electronic device may transmit video data, audio data, and/or other data to another electronic device in system 8. Bluetooth circuitry may transmit Bluetooth advertising packets and other Bluetooth packets that are received by Bluetooth receivers in nearby devices. Electronic devices in system 8 may use wired and/or wireless communications circuitry to communicate through one or more communications networks (e.g., the internet, local area networks, etc.). The communications circuitry may be used to allow data to be transmitted to and/or received by device 10 from external equipment (e.g., a tethered computer, a portable device such as a handheld device or laptop computer, online computing equipment such as a remote server or other remote computing equipment, an accessory such as a hands-free audio system in a vehicle or a wireless headset, or other electrical equipment) and/or to provide data to external equipment.

During operation, devices 10 and 20 may transmit wireless signals such as Bluetooth signals or other short-range wireless signals and may monitor for these signals from other devices.

For example, devices 10 may transmit Bluetooth signals such as Bluetooth advertising packets that are received by other devices 10. Transmitting devices 10 may sometimes be referred to as remote devices, whereas receiving devices 10 may sometimes be referred to as local devices. In transmitting Bluetooth advertisements (advertisement packets), each remote device may include information in the transmitted advertisements on the recent movement activity of that remote device and other information about the state of the remote device. Movement activity, which may sometimes be referred to as motion context, user motion information, or motion activity information, reflects the recent activities of the user of the remote device involving movement of the user's body (e.g. activities such as resting by sitting and/or standing or moving by walking, running, and/or cycling). User motion information may be sent between the electronic devices within system 8 to allow for measurement of a user's motion on multiple devices, as well as the calibration of motion sensors at each device, for example. Although Bluetooth is sometimes referred to herein as an example of sending motion information between devices, any desired protocol may be used to send motion data.

During operation, devices 10 and/or 20 may use sensors 116, wireless circuitry such as satellite navigation system circuitry, and/or other circuitry in making measurements that are used in determining a device's motion context. For example, motion data from an accelerometer and/or an inertial measurement unit may be used to identify if a user's motions (e.g., repetitive up and down motions and/or other motions with a particular intensity, a particular cadence, or other recognizable pattern) correspond to walking, running, or cycling. If desired, location information from a satellite navigation system receiver may be used in determining a user's velocity and thereby determining whether a user is or is not walking, running, or cycling. In some arrangements, the frequency with which a user's cellular telephone transceiver links to different cellular telephone towers may be analyzed to help determine the user's motion. The user's frequency of linking to or receiving signals from different wireless local area network hotspots may also be analyzed to help determine the user's motion and/or other sensor information (e.g., altimeter readings indicating changes in altitude, etc.) may be gathered and processed to determine a user's activity. These techniques and/or other techniques may be used in determining motion context.

In addition to gathering and processing sensor data and other data indicative of the user's motion context, control circuitry 112 in device 10 may, if desired, monitor whether device 10 is wirelessly linked by a short-range wireless link (e.g., via Bluetooth) to handsfree audio systems in vehicles or other vehicle equipment known to be located in or associated with vehicles. In this way, the in-vehicle status of device 10 can be determined. For example, control circuitry 112 in a given device can determine whether the given device is preset in a vehicle or not based on whether circuitry 12 is or is not wirelessly linked with an in-vehicle hands-free system.

In addition to this presence-in-vehicle state information, control circuitry 112 can determine other information about the location of device 10. As an example, control circuitry 112 can conclude that a device is indoors if the device is linked by a short-range wireless link to in-home equipment (e.g., a set-top box, television, countertop speaker, in-home desktop computer, etc.) and can determine that the device is not indoors (and is therefore outdoors) if the device is not linked to this type of in-home equipment and, if desired, sensors in the device sense one or more additional indicators of presence in an outdoors environment such as bright sunlight, etc. In general, any suitable device status information (e.g. device context such as in-vehicle states, indoor-outdoor states, etc.) may be determined by devices 10 and can potentially be shared between devices, as appropriate.

Figure 4:
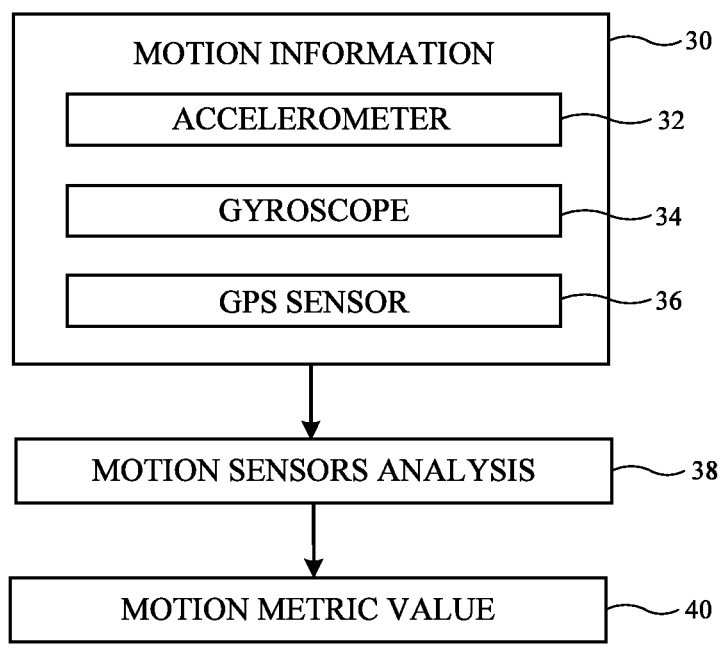
FIG. 4 is a diagram of an illustrative motion sensor apparatus and associated circuitry in accordance with an embodiment.

In some embodiments, devices 10 and/or 20 (and/or other devices within system 8) may determine motion of a user. As shown in FIG. 4, motion information 30 may be determined using one or more sensors, such as sensors 118 of device 10 or sensors 218 of device 20. Sensors 118 and/or sensors 218 may include one or more of accelerometer 32, gyroscope 34, and global positioning system (GPS) sensor 36 to measure motion information 30, as examples. Accelerometer 32 may be a two-dimensional or three-dimensional accelerometer (e.g., accelerometer 32 may measure motion in one or two directions). In some embodiments, sensors 118/218 may include other motion sensors or other sensors that may be used to detect motion more generally, such as cameras, light sensors, microphones, or other sensors. However, this is merely illustrative. In general, sensors 118 and/or sensors 218 may include any desired sensors to measure motion of the associated device.

Using data generated by the sensors that collect the motion information, control circuitry, such as control circuitry 112 of device 10, may perform a motion sensor analysis 38 by analyzing the data generated by the one or more sensors. For example, the control circuitry may compare the data generated by each sensor and fuse the data to determine a motion metric value 40. This may be done statistically through weighting, removing outlier measurements from the set, averaging the data, or any other desired method. Motion metric value 40 may be stored within the storage circuitry of the electronic device.

In general, the sensors used to calculate motion metric value 40 may automatically obtain updated motion data at any desired time interval and/or be manually triggered by actions of a user. In either case, the motion metric value 40 may be updated and logged within the storage circuitry when there is enough data to calculate the metric value. Additionally, in some cases, third parties, such as healthcare providers, may adjust the period in which data is collected and used to calculate the metric value. For example, if a user undergoes an event that could abruptly change their health/fitness capacities, such as an injury or surgery, the user's healthcare provider could reset the data collection period such that motion metric value 40 does not consider data from before the incident/event. In this way, device 10 may calculate motion metric value 40 once a requisite amount of data is collected from the previous motion metric value 40 calculation, or from the third party provider data reset time, whichever is later. This may ensure more accurate motion metric calculations for users who undergo events that reduce their fitness capacity.

Figure 5:
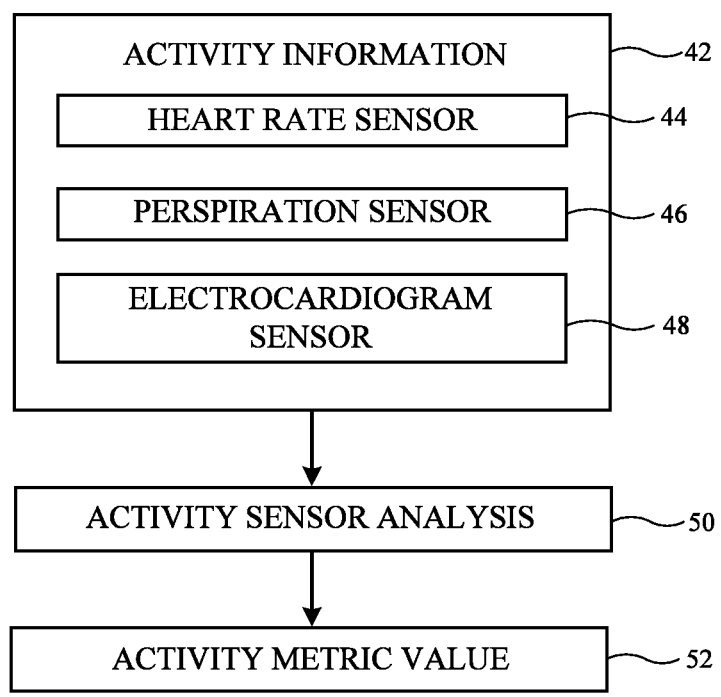
FIG. 5 is a diagram of an illustrative activity sensor apparatus and associated circuitry in accordance with an embodiment.

In addition to calculating the motion of the device, sensors with electronic device 10 and/or device 20 may determine activity information of the user. As shown in FIG. 5, activity information 42 may be determined using one or more sensors, such as sensors 118 of device 10 or sensors 218 of device 20. Sensors 118 and/or sensors 218 may include one or more of heart rate sensor 44, perspiration sensor 46, and electrocardiogram (EKG) sensor 48 to measure activity information 42, as examples. These sensors may also be used in conjunction with the motion sensors described in connection with FIG. 4 to further obtain activity information, if desired.

Using data generated by the activity information sensors (and the motion information sensors, if desired), control circuitry, such as control circuitry 112 of device 10, may perform an activity sensor analysis 50 by analyzing the data generated by the one or more sensors. For example, the control circuitry may compare the data generated by each sensor and fuse the data to determine an activity metric value 52. This may be done statistically through weighting, removing outlier measurements from the set, averaging the data, or any other desired method. Activity metric value 52 may be stored within the storage circuitry of the electronic device.

In general, the sensors used to calculate activity metric value 52 may automatically obtain updated motion data at any desired time interval and/or be manually triggered by actions of a user. In one example, the electronic device may be placed into an exercise mode, in which the activity information sensors and/or the motion sensors are activated more frequently to determine the user's biometric information more often. In any case, the activity metric value 52 may be updated and logged within the storage circuitry when there is enough data to calculate the metric value. Additionally, in some cases, third parties, such as healthcare providers, may adjust the period in which data is collected and used to calculate the metric value. For example, if a user undergoes an event that could abruptly change their health/fitness capacities, such as an injury or surgery, the user's healthcare provider could reset the data collection period such that activity metric value 52 does not consider data from before the incident/event. In this way, device 10 may calculate activity metric value 52 once a requisite amount of data is collected from the previous activity metric value 52 calculation, or from the third party provider data reset time, whichever is later. This may ensure more accurate activity metric calculations for users who undergo events that reduce their fitness capacity.

Figure 6:
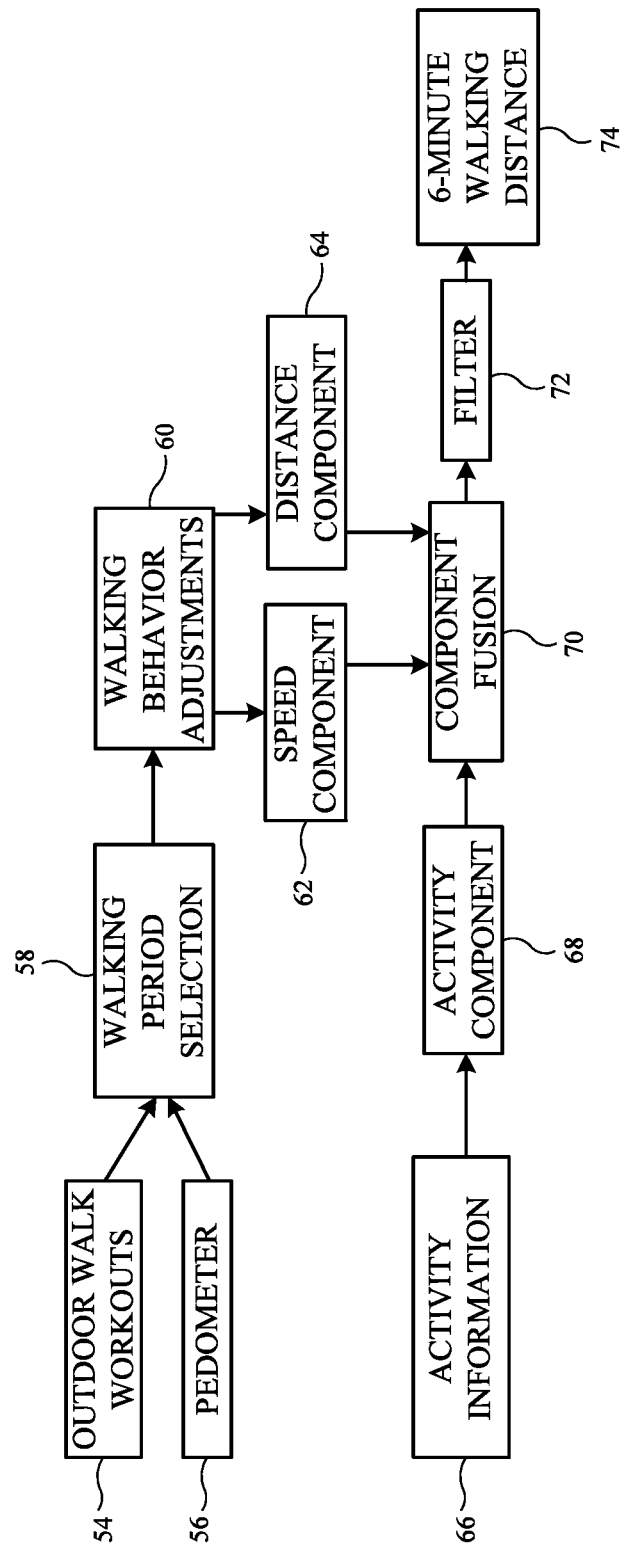
FIG. 6 is a diagram of illustrative components used by control circuitry to estimate a 6 minute walking distance in accordance with an embodiment.

Based on the motion metric value, the activity metric value, and any other desired values, control circuitry within the electronic device, such as control circuitry 112 of device 10, may estimate a 6 minute walking distance for the user. As shown in FIG. 6, information regarding outdoor walk workouts 54 and pedometer information 56 (e.g., information related to indoor walk workouts) may be used. This information may be derived from motion metric value 40 and/or activity metric value 52. In general, using the sensors described with FIGS. 3-5, the one or more electronic devices may determine that a user has walked, either inside or outside, based on their motion and activity.

Control circuitry may analyze the inside and outside walking data to select walking periods (which also may be referred to as bouts herein) that may be used to estimate the user's 6 minute walking distance. In one example, the control circuitry may select walking periods that are over two minutes, in which the user is not running, with the longest distances. However, this is merely illustrative. In general, any walking periods may be used to estimate the user's 6 minute walking distance. For example, if a user does not have sufficient data to satisfy walking periods over two minutes, shorter time periods may be used.

Each of the selected walking periods may have a distance component and a speed component. The distance component may be based on a user's cadence and step length, which may be measured using either motion information sensors 30 (also referred to as inertial sensors herein) and/or GPS sensors in one or both of a wristwatch (such as device 10) and a phone in the user's pocket (such as device 20). In the absence of GPS data to determine the distance a user walks, the user's height, BMI, and age may be used to estimate the step length of the user, and the motion sensors may be used to determine the number of steps the user takes, and thereby estimate a distance walked. The distance component may be direct evidence of the distance that a user can walk in 6 minutes, particularly if the user has completed six minute walks. In the absence of completed six minute walks, the distance data may be extrapolated.

The speed component is based on the user's speed in walking periods less than six minutes in length. The speed may be extrapolated to estimate how far a user may have walked in six minutes. This is because the user's speed is related to their lower limb muscle strength. Observations of higher speeds during short walking periods may indicate that a user is not limited by the strength of their lower limb muscles, and their time in the short period may be extrapolated to predict the 6 minute walk distance assuming sufficient endurance and fitness. The extrapolation may be calculated using a linear regression (or any other desired statistical analysis) across all walking periods or only on walking periods that meet certain criteria, such as walking periods that are reflective of the highest measured distances for the user.

Figure 7A:
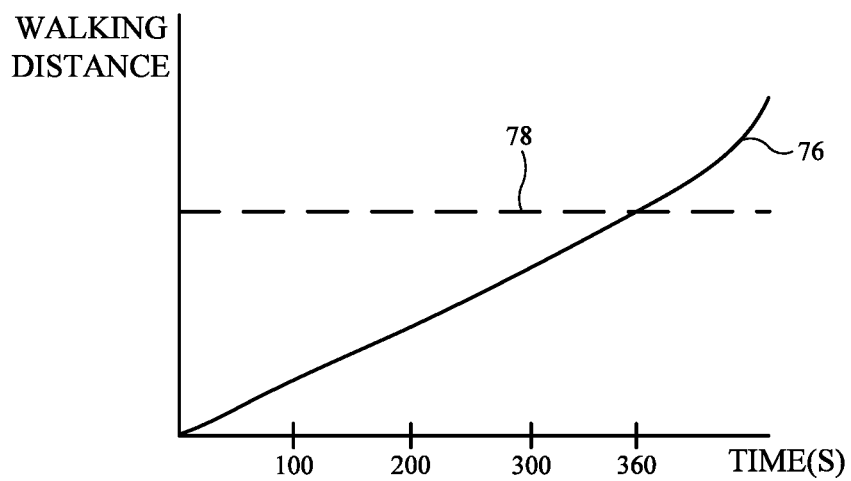
FIGS. 7A and 7B are graphs of illustrative relationships between walking distance and time for more active and more idle users in accordance with an embodiment.
Figure 7B:
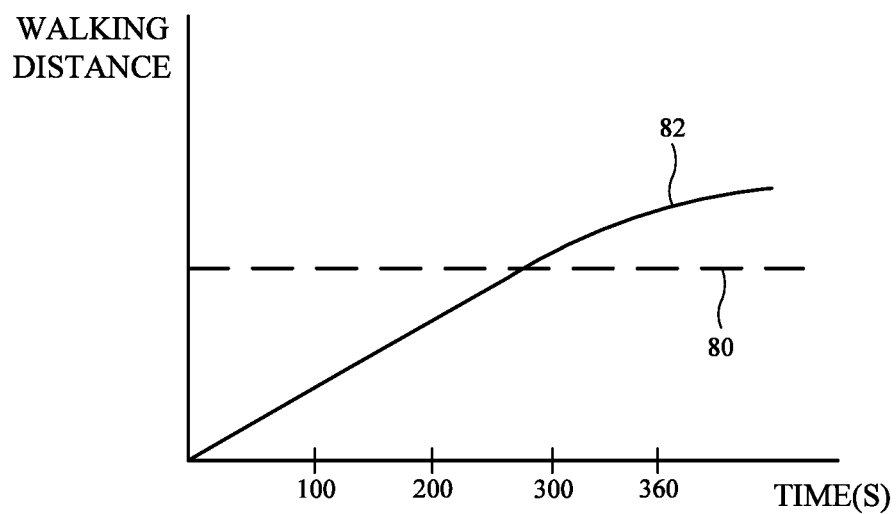

The speed component's relation to walking distance is illustrated in FIGS. 7A and 7B. In FIG. 7A, the walking distance over time is illustrated for an active user by line 76 (extrapolated to 6 minutes). As shown, the distance traveled increases with increasing time, even at the end of the six minute time period. As a result, an extrapolation of the user's speed 76 may reasonably align with the actual walking distance over the 6 minute period, which is illustrated by line 78. On the other hand, the walking distance over time is illustrated for a more idle user by line 82. As shown, the extrapolation of the user's walking distance is much higher than their actual walking distance, which is illustrated by line 80. Therefore, the user's speed may be weighted if the user is more idle (e.g., if data collected by the motion and/or activity sensors indicates that the user performs fewer workouts, walks less often or for shorter distances, burns fewer daily calories, etc.), which may allow for better approximations of the user's 6 minute walk distance when combined with the distance component.

After the walking periods of interest have been selected, the data from each of the walking periods (e.g., the distance component and the speed component of each walking period) may be adjusted using walking behavior adjustments 60, as shown in FIG. 6. As previously discussed, the walking conditions for a user under general conditions may not parallel a six minute walk indoors, on flat ground, with the required length and turns, and with maximum effort on the part of the user. However, various walking behaviors may be identified by the sensors within the electronic device to correct the walking period data.

In one example, a user may pause mid-walk. Mid-walk pauses may indicate that the user is fatigued, or is experiencing an interruption in walking, such as a stop light or an interaction with another person. These pauses may be indicated by lack of data indicating motion from the motion information sensors 30 of FIG. 4. To compensate for mid-walk interruptions, the control circuitry may filter our walking periods with pauses if pauses are not commonly observed in the user's typical walking periods of similar or higher durations. Additionally, if pauses occur in street intersections, as determined by the device's GPS location, walking periods with pauses may be filtered out. However, if pauses occur more frequently during the user's walks or are longer in duration as walking period times increase between 30 seconds and 6 or more minutes, the pauses may be maintained in the walking period data. This is because more frequent pauses may indicate that the user is pausing due to fatigue, rather than due to environmental factors.

In another example, a grade may be detected by the electronic device. A grade may be detected by various sensors within the device, such as accelerometer 32, gyroscope 34, a barometer, or any other desired sensors. Walking grade may not be reflective of the distance captured during 6 minute walking distance tests performed in clinical settings. To compensate for grading, walking periods with grades over 2% may be excluded. Alternatively or additionally, some or all walking periods with grading may be normalized with a grade correction factor to estimate the distance that the user would have walked on flat ground.

In a third example, a user may walk on a non-linear walking path, which may be determined by one or more of the motion information sensors 30 of FIG. 4. Because the 6 minute walking distance test is often conducted on 30 meter straightaways (or other fixed distance, such as 20 meters) in the clinical setting, the non-linearity may be corrected. In particular, the user's heading may be determined using a magnetometer. If the heading frequently deviates from a straight course, the walking period may be excluded.

In another example, a user may lack 180° turns in their walk, which are present at both ends of the 30 m straightaway in clinical tests. To compensate, the 6 minute walk prediction may be adjusted based on the approximated turn time not included in the walking periods. In some examples, the walking periods may be adjusted by 10%. However, any desired correction may be applied to the walking period data.

In a further example, the user may have a constrained arm pose while walking, which may indicate that the user is holding onto something while walking, such as a stroller, a walker, or a dog leash. Users who are pushing a stroller or walking a dog may not be walking at peak capacity. To correct for arm constraint, walking periods with constrained arm poses may be excluded for users that have been observed to cover moderate to higher distances, such as more than 300 m or 350 m in six minutes. Users with lower typical distances, such as under 300 m in six minutes, may not have these walking periods excluded, as their constrained arm pose may be due to a walker. Alternatively or additionally, users may be asked to manually indicate that they use a walker, or may have the option of entering that information on the electronic device.

In another example, an assistive device, such as a cane, may be used in the completion of the 6 minute test. This may change the mechanics of walking observed from the wrist of the user. To correct for these devices, phone-based distances may be prioritized if the users have indicated that a large fraction of their walking periods are performed with an assistive device.

Another walking behavior adjustment may be in response to workout walking (e.g., when a user indicates that they are working out prior to the walking period). In particular, this may indicate that the user will use increased effort during the workout, as opposed to during leisurely walking. Additionally, additional sensors, such as heartrate sensor 44 and GPS sensor 36 may be activated during workout walks, or may be sampled more regularly. In response to these workout walks, the corresponding walking periods may be weighted higher, especially if the user's heartrate is elevated relative to normal levels of exertion.

Cadence and step length may also be corrected for during walking behavior adjustments 60. In particular, some environments may cause users to adopt atypical walking mechanics, such as taking faster but shorter steps that would not reflect their capability in a controlled environment. This may include walking in mud, sand, or snow, as examples. In other situations, an increase in cadence may indicate that the user is merely walking more briskly. These changes in behavior may be reflected in the user's cadence or step length, which may be detected by motion information sensors 30 of FIG. 4. In response to increased cadence or step length in a given walking period, the period may be excluded if it is an outlier compared to distributions amassed in the past several days, such as the past 3 days, the past 3-28 days, or some other number of days. Alternatively, walking periods with elevated cadence may be weighted higher (e.g., if the user regularly walks at this elevated pace to workout).

In another example, the user's speed may change in the middle of a walking period. When a user's speed consistently declines over longer durations of walking, this may indicate fatigue or reduced endurance/fitness. Alternatively, a rise in speed over time may indicate that at shorter periods, the user is deciding to walk at slower speeds. To correct for a change in speed, walking periods with significantly slowing speed, such as a drop of 30% or more (or any other desired deviation), may be weighted greater, as they may be representative of a user's maximal effort. Extrapolation of the speed component for these users should be adjusted to have a less steep regression. On the other hand, if a user has increasing speed over time, extrapolation of speed should be adjusted to have a steeper regression.

Returning to FIG. 6, after correcting the walking period data, a corrected speed component 62 and distance component 64 may be obtained. An estimated 6 minute walk distance may be calculated based on speed component 62 by extrapolating the distance based on shorter walk periods, by comparing distance measured vs. walking time. This extrapolation may be performed on all walking periods, or may occur only on walking periods that meet certain criteria, such as walking periods that are among the highest measured distances.

The distance component may be similarly be used to estimate a 6 minute walk distance. In particular, the estimated distance may be based on a percentile of all walking periods, such as a $98^{th}$ percentile; a percentile of walking periods greater than a certain duration, such as a $90^{th}$ percentile of walking periods greater than 4 minutes or greater than 6 minutes; or a weighted average of walking periods of at least a given period of time, such as a 330 second period. However, these estimation techniques are merely illustrative. In general, any statistical analysis of the distance component may be used to estimate a 6 minute walking distance.

Figure 8:
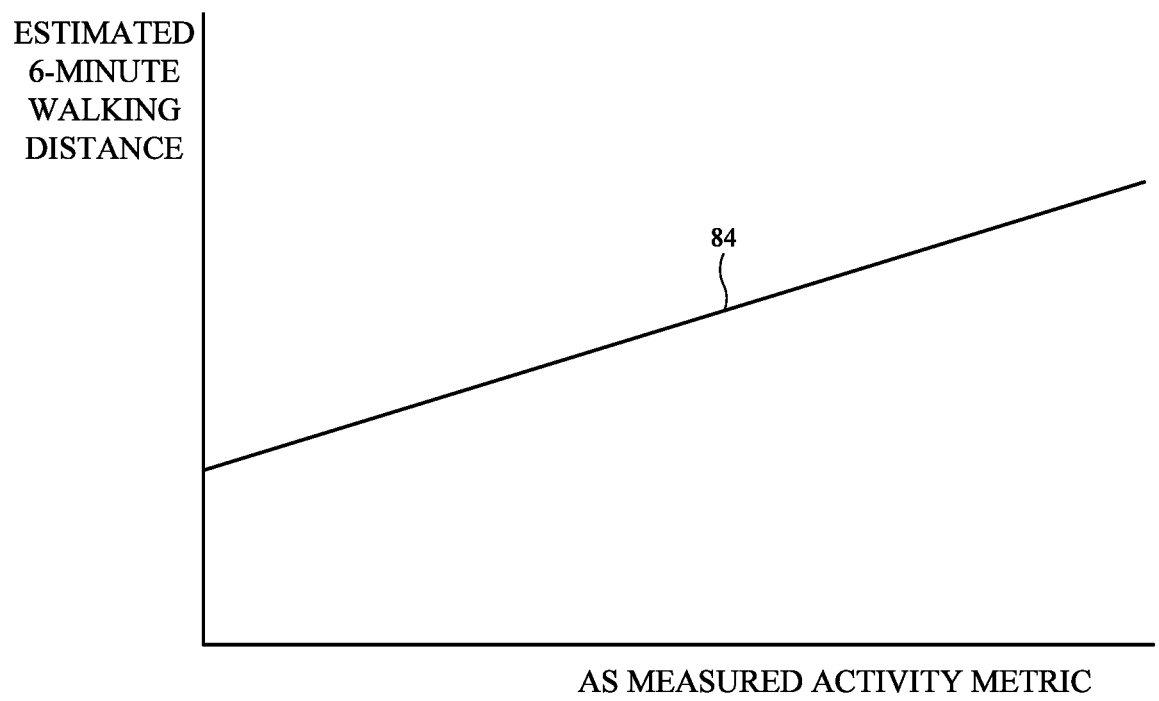
FIG. 8 is a graph of an illustrative relationship between a measured activity metric and an estimated 6 minute walking distance in accordance with an embodiment.

In parallel with obtaining and correcting the walking period data, activity information 66 may be obtained. Activity information 66 may include broader information than the individual walking periods discussed in connection with outdoor walk workouts 54 and pedometer data 56. For example, activity information 66 may include data on calories expended by the user, standing hours and/or standing minutes, flights of stairs climbed, workouts completed, and ascent and descent rate of stairs, as examples. However, other activity information may be included, if desired. This data may be obtained using one or more of accelerometer 32, gyroscope 34, GPS sensor 36, hear rate sensor 44, a barometer, and any other desired sensors and may be stored within electronic device 10 and/or electronic device 20. The data may be statistically combined using any desired method, such as regression, random forest, or decision tree methods, to form activity component 68 (also referred to as an activity metric herein). As illustrated by line 84 in FIG. 8, the activity metric may be represented using a linear relationship (disregarding noise in the system) with the estimated 6 minute walking distance following a regression or other statistical analysis. In this way, an estimated 6 minute walking distance may be determined based on the activity metric.

After speed component 62, distance component 64, and activity component 68 have been determined and the 6 minute walking distance estimates calculated based on each component, all three estimates may be statistically combined at component fusion 70. In particular, the three estimates may be statistically combined along with any other desired features, such as relevant health data (e.g., maximal calories burned over the last 1-4 weeks). In one example, the estimates may be statistically combined using a decision tree that chooses or discounts (e.g., weights) a component's estimate based on evidence from the other components. For example, the decision tree may select the single most accurate one of the component estimates to serve as the 6 minute walking estimate. Alternatively, the distance component estimate may be adjusted based on the speed and activity components, along with independent fitness measurements, such as calories burned.

Filter 72 may ensure that enough data has been collected to accurately estimate the 6 minute walking distance. In general, filter 72 may determine whether the estimates generated by the distance, speed, and activity components sufficiently correlate and whether a threshold of data points have been collected. Assuming that the conditions of filter 72 are met, the fused estimate of the user's 6 minute walking distance may be output and stored in the device's circuitry.

Figure 9:
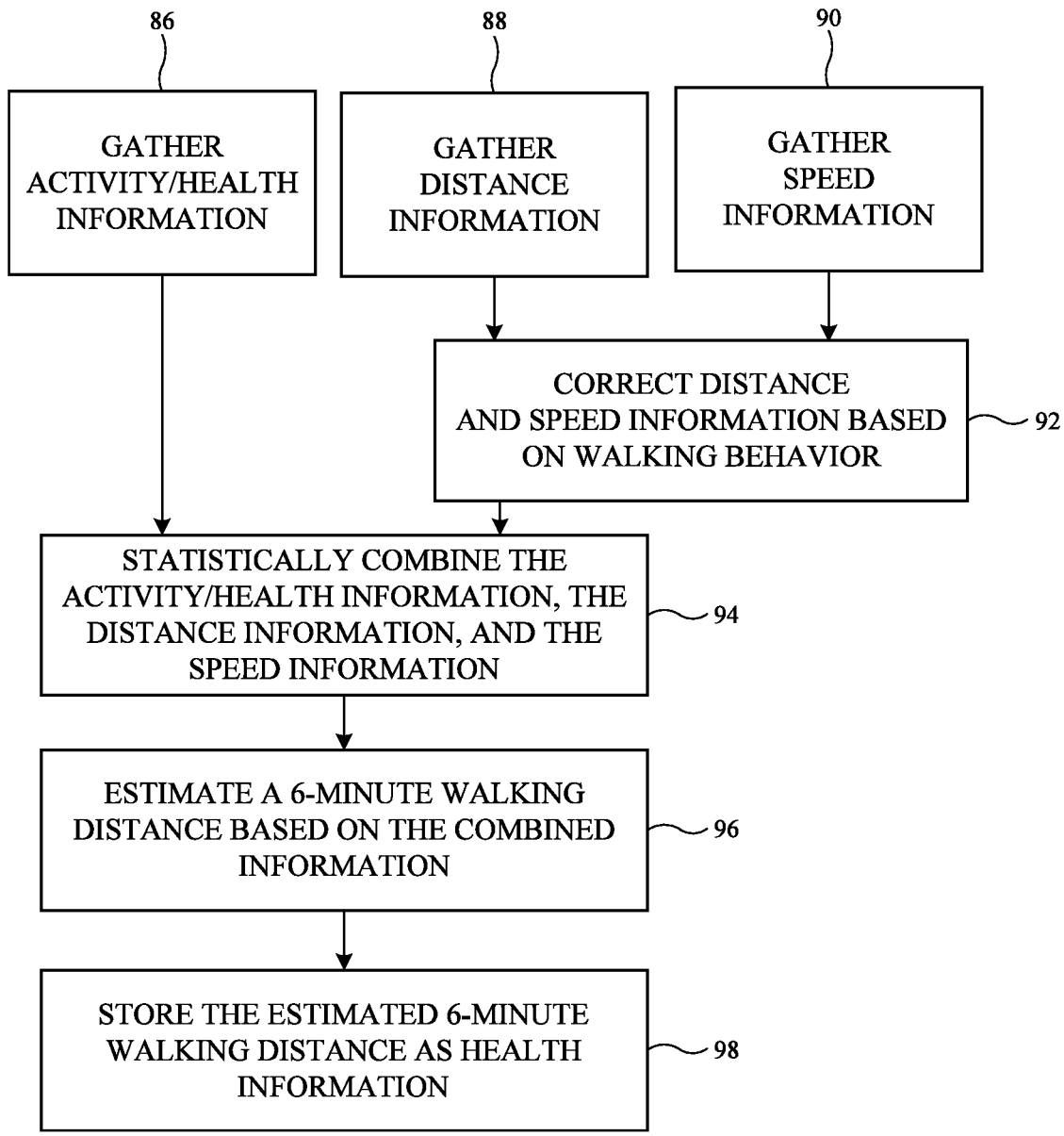
FIG. 9 is a flowchart of illustrative steps used to estimate a 6 minute walk time in accordance with an embodiment.

A flowchart illustrating the steps performed in connection with the diagram of FIG. 6 is shown in FIG. 9. At step 86, the electronic device(s) (device 10, device 20, and/or any other desired device) may obtain activity/health information. The activity information may include data on calories expended by the user, standing hours and/or standing minutes, flights of stairs climbed, workouts completed, ascent and descent rate of stairs, and any other desired activity information. This data may be obtained using one or more of accelerometer 32, gyroscope 34, GPS sensor 36, hear rate sensor 44, a barometer, and any other desired sensors and may be stored within electronic device 10 and/or electronic device 20. The data may be statistically combined using any desired method, such as regression, random forest, or decision tree methods, to form an activity component. A 6 minute walk distance may be estimated based on this activity component (e.g., based on previous statistical regression to determine a relationship between the activity component and the 6 minute walk distance).

In parallel with step 86, at step 88, the electronic device(s) (device 10, device 20, and/or any other desired device) may obtain distance information. The distance information may be obtained from motion sensors, such as motion information sensors 30, activity sensors, such as activity information sensors 42, and/or any other desired sensors. In particular, the sensors may determine when a user has walked, and the distance of any detected walks. The device may discard distance information that does not meet pre-selected criteria, such as the walk being over two minutes and not being a run, as examples.

After the distance information has been reduced to the desired data set, the distance information may be used to estimate a 6 minute walking distance. In particular, the estimated distance may be based on a percentile of all walking periods, such as a $98^{th}$ percentile; a percentile of walking periods greater than a certain duration, such as a $90^{th}$ percentile of walking periods greater than 4 minutes or greater than 6 minutes; or a weighted average of walking periods of at least a given period of time, such as a 330 second period. In some examples, the estimated 6 minute walking distance may be extrapolated from the walking periods that have been selected. However, these estimation techniques are merely illustrative. In general, any statistical analysis of the distance component may be used to estimate a 6 minute walking distance.

In parallel with steps 86 and 88, at step 90, the electronic device(s) (device 10, device 20, and/or any other desired device) may obtain speed information. The speed information may be obtained from motion sensors, such as motion information sensors 30, and/or any other desired sensors. In particular, the sensors may determine the user's speed over the time period for any detected walk. The device may discard distance information that does not meet pre-selected criteria, such as the walk being over two minutes and not being a run, as examples.

After the speed information has been reduced to the desired data set, the speed information may be used to estimate a 6 minute walking distance. In particular, an estimated 6 minute walk distance may be calculated based on the speed component by extrapolating the distance based on shorter walk periods, by comparing distance measured vs. walking time. This extrapolation may be performed on all walking periods, or may occur only on walking periods that meet certain criteria, such as walking periods that are among the highest measured distances.

After the distance and speed components have been determined, at step 92, the distance and speed components may be corrected based on walking behavior. For example, the 6 minute walking estimates that have been calculated for the distance and speed components may be adjusted based on determinations that the user has paused, walked on a grade, taken a non-linear walking path, not turned 180°, had a constrained arm pose, was working out, had an atypical cadence and/or step length, and/or changed speed during the walking period. In this way, the distance and speed components may be corrected to better approximate the conditions under which the user would perform the 6 minute walking distance test in a clinical environment.

At step 94, the estimates based on the activity/health information, the corrected distance information, and the corrected speed information may be statistically combined. In particular, the three estimates may be statistically combined along with any other desired features, such as relevant health data (e.g., maximal calories burned over the last 1-4 weeks). In one example, the estimates may be statistically combined using a decision tree that chooses or discounts a component's estimate based on evidence from the other components. Alternatively, the distance component estimate may be adjusted based on the speed and activity components, along with independent fitness measurements, such as calories burned.

At step 96, a 6 minute walking distance may be estimated based on the combined information. In particular, the circuitry may filter the combined information to ensure that the estimates generated by the distance, speed, and activity components sufficiently correlate and whether a threshold of data points have been collected. Assuming that the conditions of the filter are met, the fused estimate of the user's 6 minute walking distance may be generated.

At step 98, the estimated 6 minute walking distance may be stored as health information. This 6 minute walking distance may be stored with previous estimations of the distance, may be presented to a user in histograms of data, may be sent to a doctor's office, may trigger an alert to the user or to a physician, may be used by other applications on electronic device 10, electronic device 20, and/or any other desired device, or may be used in any other desired fashion.

As described above, one aspect of the present technology is the gathering and use of information such as information from input-output devices. The present disclosure contemplates that in some instances, data may be gathered that includes personal information data that uniquely identifies or can be used to contact or locate a specific person. Such personal information data can include demographic data, location-based data, telephone numbers, email addresses, twitter ID's, home addresses, data or records relating to a user's health or level of fitness (e.g., vital signs measurements, medication information, exercise information), date of birth, username, password, biometric information, or any other identifying or personal information.

The present disclosure recognizes that the use of such personal information, in the present technology, can be used to the benefit of users. For example, the personal information data can be used to deliver targeted content that is of greater interest to the user. Accordingly, use of such personal information data enables users to calculated control of the delivered content. Further, other uses for personal information data that benefit the user are also contemplated by the present disclosure. For instance, health and fitness data may be used to provide insights into a user's general wellness, or may be used as positive feedback to individuals using technology to pursue wellness goals.

The present disclosure contemplates that the entities responsible for the collection, analysis, disclosure, transfer, storage, or other use of such personal information data will comply with well-established privacy policies and/or privacy practices. In particular, such entities should implement and consistently use privacy policies and practices that are generally recognized as meeting or exceeding industry or governmental requirements for maintaining personal information data private and secure. Such policies should be easily accessible by users, and should be updated as the collection and/or use of data changes. Personal information from users should be collected for legitimate and reasonable uses of the entity and not shared or sold outside of those legitimate uses. Further, such collection/sharing should occur after receiving the informed consent of the users. Additionally, such entities should consider taking any needed steps for safeguarding and securing access to such personal information data and ensuring that others with access to the personal information data adhere to their privacy policies and procedures. Further, such entities can subject themselves to evaluation by third parties to certify their adherence to widely accepted privacy policies and practices. In addition, policies and practices should be adapted for the particular types of personal information data being collected and/or accessed and adapted to applicable laws and standards, including jurisdiction-specific considerations. For instance, in the United States, collection of or access to certain health data may be governed by federal and/or state laws, such as the Health Insurance Portability and Accountability Act (HIPAA), whereas health data in other countries may be subject to other regulations and policies and should be handled accordingly. Hence different privacy practices should be maintained for different personal data types in each country.

Despite the foregoing, the present disclosure also contemplates embodiments in which users selectively block the use of, or access to, personal information data. That is, the present disclosure contemplates that hardware and/or software elements can be provided to prevent or block access to such personal information data. For example, the present technology can be configured to allow users to select to "opt in" or "opt out" of participation in the collection of personal information data during registration for services or anytime thereafter. In another example, users can select not to provide certain types of user data. In yet another example, users can select to limit the length of time user-specific data is maintained. In addition to providing "opt in" and "opt out" options, the present disclosure contemplates providing notifications relating to the access or use of personal information. For instance, a user may be notified upon downloading an application ("app") that their personal information data will be accessed and then reminded again just before personal information data is accessed by the app.

Moreover, it is the intent of the present disclosure that personal information data should be managed and handled in a way to minimize risks of unintentional or unauthorized access or use. Risk can be minimized by limiting the collection of data and deleting data once it is no longer needed. In addition, and when applicable, including in certain health related applications, data de-identification can be used to protect a user's privacy. De-identification may be facilitated, when appropriate, by removing specific identifiers (e.g., date of birth, etc.), controlling the amount or specificity of data stored (e.g., collecting location data at a city level rather than at an address level), controlling how data is stored (e.g., aggregating data across users), and/or other methods.

Therefore, although the present disclosure broadly covers use of information that may include personal information data to implement one or more various disclosed embodiments, the present disclosure also contemplates that the various embodiments can also be implemented without the need for accessing personal information data. That is, the various embodiments of the present technology are not rendered inoperable due to the lack of all or a portion of such personal information data.

The foregoing is illustrative and various modifications can be made to the described embodiments. The foregoing embodiments may be implemented individually or in any combination.

Table of Reference Numerals

| 10, 20 | Electronic Devices | 12, 22 | Housings |
| 14, 24 | Displays | 16 | Watch Band |
| 8 | System | 112, 212 | Control Circuitry |
| 114, 214 | Communications Circuitry | 116, 216 | Input-Output Devices |
| 118, 218 | Sensors | 122, 222 | Other Devices |
| 30 | Motion Information | 32 | Accelerometer |
| 34 | Gyroscope | 36 | GPS Sensor |
| 38 | Motion Sensor Analysis | 40 | Motion Metric Value |
| 42 | Activity Information | 44 | Heart Rate Sensor |
| 46 | Perspiration Sensor | 48 | Electrocardiogram Sensor |
| 50 | Activity Sensor Analysis | 52 | Activity Metric Value |
| 54 | Information regarding Outdoor Walk Workouts | 56 | Pedometer Information |
| 58 | Walking Period Selection | 60 | Walking Behavior Adjustments |

Table of Reference Numerals (continued)

| 62 | Speed Component | 64 | Distance Component |
| 66 | Activity Information | 68 | Activity Component |
| 70 | Component Fusion | 72 | Filter |
| 74 | 6 Minute Walk Distance | 76, 78, 80, 82, 84 | Lines |
| 86, 88, 90, 92, 94, 96, 98 | Flowchart Steps | | |

What is claimed is:

1. An electronic device configured to be worn by a user, the electronic device comprising:
   a housing;
   a first sensor that measures a motion of the housing;
   a second sensor that measures a heart rate of the user; and
   control circuitry configured to:
   determine walking periods based on the motion of the housing, wherein each of the walking periods has a distance component and a speed component;
   determine activity information based on the heart rate of the user and the motion of the housing; and
   calculate a 6 minute walk distance for the user as a function of the distance component, the speed component, and the activity information.

2. The electronic device defined in claim 1 wherein the control circuitry is further configured to produce a distance estimate of the 6 minute walk distance based on the distance component, to produce a speed estimate of the 6 minute walk distance based on the speed component, and to produce an activity estimate of the 6 minute walk distance based on the activity information.

3. The electronic device defined in claim 2 wherein the control circuitry is configured to determine walking behaviors of the user during the walking periods using the first sensor and wherein the control circuitry is configured to correct the distance estimate and the speed estimate based on the walking behaviors.

4. The electronic device defined in claim 3 wherein the walking behaviors are selected from the group consisting of: a pause, a graded walking path, a non-linear walking path, a lack of 180° turns, a constrained arm pose, an assistive device usage, a workout, an atypical cadence, an atypical step length, and a speed change.

5. The electronic device defined in claim 3 wherein the control circuitry is configured to determine the 6 minute walk distance by statistically combining the corrected distance estimate, the corrected speed estimate, and the activity information.

6. The electronic device defined in claim 1 wherein the electronic device is a wristwatch device having a display and communications circuitry, and wherein the communications circuitry is configured to communicate with an external electronic device.

7. The electronic device defined in claim 6 wherein the control circuitry is configured to calibrate the first sensor based on information received from the external electronic device.

8. The electronic device defined in claim 1 wherein the first sensor is an accelerometer and wherein the electronic device further comprises:
   a gyroscope and a global positioning system sensor that measure additional aspects of the motion of the housing, wherein the control circuitry is configured to analyze data from the accelerometer, the gyroscope, and the global positioning system sensor to determine the walking periods.

9. The electronic device defined in claim 8 wherein the second sensor is a heart rate sensor, wherein the electronic device further comprises:
a perspiration sensor, wherein the control circuitry is configured to determine the activity information based on the heart rate of the user and data from the perspiration sensor.

10. The electronic device defined in claim 9 wherein the heart rate sensor is a photoplethysmography sensor, wherein the electronic device further comprises an electrocardiogram sensor, and wherein the control circuitry is configured to determine the activity information based on data from the photoplethysmography sensor, the data from the perspiration sensor, and data from the electrocardiogram sensor.

11. The electronic device defined in claim 1 wherein the activity information includes calorie expenditure data of the user, standing time, and stair ascent and descent data.

12. The electronic device defined in claim 1 wherein the control circuitry is further configured to produce a distance estimate of the 6 minute walk distance based on the distance component by extrapolating the distance estimate from a selected percentile of all periods in which the user has walked.

13. The electronic device defined in claim 12 wherein the control circuitry is further configured to produce a speed estimate of the 6 minute walk distance by extrapolating a speed of the user within selected walking periods that are shorter than six minutes to estimate the distance that the user could have traveled in the six minutes.

14. The electronic device defined in claim 1 wherein the control circuitry is further configured to produce a distance estimate of the 6 minute walk distance based on the distance component, to produce a speed estimate of the 6 minute walk distance based on the speed component, and to produce an activity estimate of the 6 minute walk distance based on the activity information, to weight each of the distance estimate, the speed estimate, and the activity estimate, and to combine the distance estimate, the speed estimate, and the activity estimate to determine the 6 minute walk distance.

15. The electronic device defined in claim 1 wherein the control circuitry is further configured to produce a distance estimate of the 6 minute walk distance based on the distance component, to produce a speed estimate of the 6 minute walk distance based on the speed component, and to produce an activity estimate of the 6 minute walk distance based on the activity information, and to use a decision tree to select a single one of the distance estimate, the speed estimate, or the activity estimate to determine the 6 minute walk distance.

16. A system configured to determine a 6 minute walking distance of a user, the system comprising:
a portable electronic device, comprising:
a first housing;
a set of first motion information sensors that generate first motion data in response to movement of the first housing; and
first communications circuitry; and
a wearable electronic device, comprising:
a second housing;
a second set of motion information sensors that generate second motion data in response to movement of the second housing;
a set of activity information sensors that generate heart rate data in response to a heart rate of the user;
second communications circuitry that is configured to receive the first motion data from the first communications circuitry; and
control circuitry, configured to:
calibrate the second set of motion information sensors based on the first motion data, and
estimate the 6 minute walking distance based on the first motion data, the second motion data, and the heart rate data.

17. The system of claim 16 wherein the wearable electronic device is a device selected from the group consisting of: a wristwatch, a headphone, an ear bud, and a head-mounted device.

* * * * *